United States Patent
Vidal et al.

[11] Patent Number: 6,165,229
[45] Date of Patent: Dec. 26, 2000

[54] IMIDAZOLOAZOLE-CONTAINING COMPOSITIONS FOR DYEING KERATIN FIBERS; THEIR USE IN DYEING AS COUPLERS; DYEING PROCESS

[75] Inventors: Laurent Vidal, Paris; Gérard Malle, Villiers sur Morin, both of France

[73] Assignee: L'Oreal, Paris, France

[21] Appl. No.: 09/155,193

[22] Filed: Feb. 8, 1999

[30] Foreign Application Priority Data

Mar. 22, 1996 [FR] France .................................... 96 03628

[51] Int. Cl.$^7$ .................................................. A61K 7/13
[52] U.S. Cl. ........................................ 8/409; 8/423; 8/573
[58] Field of Search ................................. 8/409, 423, 573

[56] References Cited

U.S. PATENT DOCUMENTS

| | | | |
|---|---|---|---|
| 3,061,432 | 10/1962 | Menzel et al. | 430/376 |
| 3,227,554 | 1/1966 | Barr et al. | 430/382 |
| 3,419,391 | 12/1968 | Young | 430/387 |
| 3,725,067 | 4/1973 | Bailey et al. | 430/476 |
| 3,820,948 | 6/1974 | Berth | 8/409 |
| 3,926,631 | 12/1975 | Arai et al. | 430/226 |
| 4,128,425 | 12/1978 | Greenwald | 430/440 |
| 4,293,543 | 10/1981 | Cotte et al. | 8/405 |
| 4,500,630 | 2/1985 | Sato et al. | 430/386 |
| 5,256,526 | 10/1993 | Suzuki et al. | 430/384 |
| 5,441,863 | 8/1995 | Tang et al. | 430/558 |
| 5,457,210 | 10/1995 | Kim et al. | 548/262.4 |

FOREIGN PATENT DOCUMENTS

| | | |
|---|---|---|
| 0 030 680 | 6/1981 | European Pat. Off. . |
| 0 119 860 | 9/1984 | European Pat. Off. . |
| 0 285 274 | 10/1988 | European Pat. Off. . |
| 0 304 001 | 2/1989 | European Pat. Off. . |
| 0 309 652 | 4/1989 | European Pat. Off. . |
| 0 320764 | 6/1989 | European Pat. Off. . |
| 0 456 226 | 11/1991 | European Pat. Off. . |
| 0 488 248 | 6/1992 | European Pat. Off. . |
| 0 488 909 | 6/1992 | European Pat. Off. . |
| 0 518 238 | 12/1992 | European Pat. Off. . |
| 0 547 864 | 6/1993 | European Pat. Off. . |
| 0 557 851 | 9/1993 | European Pat. Off. . |
| 0 578 248 | 1/1994 | European Pat. Off. . |
| 0 591 103 | 4/1994 | European Pat. Off. . |
| 1 564 999 | 4/1969 | France . |
| 2 075 583 | 10/1971 | France . |
| 2 466 492 | 4/1981 | France . |
| 2 486 913 | 3/1987 | France . |
| 2 160 317 | 6/1973 | Germany . |
| 2 359 999 | 6/1975 | Germany . |
| 3 731 395 | 4/1989 | Germany . |
| 3 843 892 | 6/1990 | Germany . |
| 4 009 097 | 9/1991 | Germany . |
| 4 133 957 | 4/1993 | Germany . |
| 58-42045 | 3/1983 | Japan . |
| 59-99437 | 6/1984 | Japan . |
| 59-071956 | 9/1984 | Japan . |
| 59-162548 | 9/1984 | Japan . |
| 60-33552 | 2/1985 | Japan . |
| 60 43659 | 3/1985 | Japan . |
| 60 172982 | 9/1985 | Japan . |
| 60 190779 | 9/1985 | Japan . |
| 62 279337 | 12/1987 | Japan . |
| 63 169571 | 7/1988 | Japan . |
| 62 36011 | 8/1994 | Japan . |
| 7-36159 | 2/1995 | Japan . |
| 7-84348 | 3/1995 | Japan . |
| 7-92632 | 4/1995 | Japan . |
| 1 026 978 | 3/1963 | United Kingdom . |
| 1 153 196 | 6/1966 | United Kingdom . |
| 1 458 377 | 9/1974 | United Kingdom . |
| WO 92/04349 | 3/1992 | WIPO . |
| WO 92/04883 | 4/1992 | WIPO . |
| WO 94/04130 | 3/1994 | WIPO . |
| WO 94-89970 | 4/1994 | WIPO . |
| WO 94/08959 | 4/1994 | WIPO . |
| WO 94/08969 | 4/1994 | WIPO . |

OTHER PUBLICATIONS

Caplus Abstract of JP 62–279,337, Konica Co., Dec. 1987.
R. Stollé, "Ueber die Ueberführung der secundären Säurehydrazide in Derivate des Furodiazols, Pyrrodiazols and Thiodiazols", Chemischen Gesellschaft, pp. 797–798, 1899.
Hans Beyer et al., "Über die Pyrazolbildung aus α–Chloracetessigester und Thiocarbohydrazid", Chemische Berichte, pp. 2550–2555, 1956.
H. Wilde et al., "Synthese von 4H–Pyrazolo[1,5–a]benzimidazolen," Journal Für Praktische Chemie, pp. 829–836, 1984.

(List continued on next page.)

*Primary Examiner*—Caroline D. Liott
*Attorney, Agent, or Firm*—Finnegan, Henderson, Farabow, Garrett & Dunner, L.L.P.

[57] ABSTRACT

The present invention relates to a composition for dyeing keratin fibers, in particular human hair, containing, in a medium which is suitable for dyeing, at least:

as coupler, at least one compound of formula:

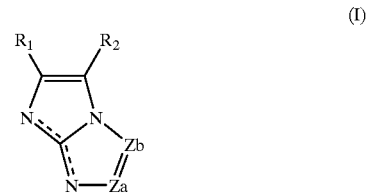

(I)

in which:

$R_1$ denotes, in particular, hydrogen, alkyl, phenyl, substituted phenyl, cyano; carbonyl; etc.

$R_2$ denotes, in particular, hydrogen, halogen, alkoxy, aryloxy, acyloxy, acetamido, dialkylamino, etc.

$Z_a$ and $Z_b$ denote a nitrogen atom or a carbon bearing a group $R_3$ or $R_4$ or $R_5$, with the proviso that at least one of the two is a carbon atom;

$R_3$ and $R_4$, which are independent, denote cyano; trifluoroalkyl; alkoxycarbonyl; aryloxycarbonyl, hydrogen; alkyl; carboxyl; etc.

$R_5$ denotes, in particular, hydrogen, aryl, alkoxy, alkylthio, etc.

at least one oxidation base.

7 Claims, No Drawings

OTHER PUBLICATIONS

Lidia Wyzgowska et al., "O Reakcjach Trikarboetoksymetanu VIII", Acta Poloniae Pharmaceutica, pp. 83–88, 1982.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Jounral f. prakt. chemie, Band 320, heft 4, pp. 533–538, 1978.

Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, 1990.

Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, vol. 109, No. 9, pp. 2711–2717, 1987.

H. Koopman, "Investigations on Herbicides IV, The synthesis of 2,6–dichlorobenzonitrile", Recueil, vol. 80, No. 9–10, pp. 1075–1083, 1961.

Joseph Bailey, "Synthesis of 1H–Pyrazolo[3,2–c]–s–Triazoles and Derived Azamethine Dyes", Journal of the chemical Society, pp. 2047–2052, 1977.

Chiara B. Vincentini et al., "Pyrazolo[3,4–d][1,2,3]Triazole–1–carboxamides and 5–Alkylaminopyrazolo[3,4–d]oxazoles: Synthesis and Evaluation of the in Vitro Antifungal Activity", Il Farmaco, vol. 47, No. 7, 8, pp. 1021–1034, 1992.

Edward C. Taylor et al., "The Reaction of Malononitrile with Substituted Hydrazines: New Routes to 4–Aminoyrazolo[3,4–d]pyrimidines", Journal of the merican Chemical Society, vol. 81, No. 10, pp. 2456–2464, 1959.

C.B. Vincentini et al., "A New fused Heterocyclic System: 6H–Pyrazolo[3,4–c][1,2,5]thiadizine 2,2–Dioxide", Journal of Heterocyclic Chemistry, vol. 26, No. 3, pp. 797–803, 1989.

E.J. Browne et al., "Triazoles. Part VII. Syntheses of Substituted 1,2,4–Triazoles", Journal of The Chemical Society, pp. 5149–5152, 1962.

von Helmut Dorn et al., "Über die elektrophile Substitution von 3(5)–Amino–pyrazol", Annalen der Chemie, pp. 141–146, 1967.

Mohamed Helmi Elnagdi et al., "Studies on 3,5–pyrazolidinediones. IV. Addition of 4–Arylazo–3–5–pyrazolidinediones to Ethyl Acrylate", Bulletin of Them Chemical Society of Japan, vol. 46, pp. 1830–1833, 1973.

Günther Ege et al., "A Simple Synthesis of 3(5)–Aminopyrazole", Angew. Chem. interant. Edit, vol. 13, No. 3, pp. 206–207, 1974.

Kazumasa Takahashi et al., "Syntheses of 3(5)–Substituted–4–(N–methylanilino)–5(3)–aminopyrazoles by Reaction of β–Hydroxy–α–cyano–enamines with Hydrazines", Journal of Synthetic Organic Chemistry, No. 8, pp. 794–796, 1985.

E. Hanning et al., "Zur Kenntnis des 4–aminierten Phenylbutazons", Die Pharmazie, pp. 231, 1980.

Giuliana Cardillo et al., "Su due constituenti minori della Kamala", Gazetta Chimica Italiana, pp. 725–734, 1965.

Thomas Kauffmann et al., "Synthese von Amidrazonon aus Nitrilen und Natriumhydrazid", pp. 3436–3443, 1964.

von Helmut Dorn et al., "Synthese und Methylierung von 1H–Pyrazolo[3,4–b]pyrazinen, einer neuen Klasse von Purin–Antagonisten", Annalen der Chemie, pp. 118–123, 1968.

IMIDAZOLOAZOLE-CONTAINING COMPOSITIONS FOR DYEING KERATIN FIBERS; THEIR USE IN DYEING AS COUPLERS; DYEING PROCESS

The invention relates to a composition for the oxidation dyeing of keratin fibres, in particular human hair, containing at least one imidazoloazole compound as coupler and at least one oxidation base.

It is known to dye keratin fibres, and in particular human hair, with dye compositions containing oxidation dye precursors, in particular ortho- or para-phenylene diamines, ortho- or para-aminophenols, and heterocyclic compounds, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is known that the shades obtained with these oxidation bases can be varied by combining them with couplers or colour modifiers, the latter being chosen in particular from aromatic meta-diamines, meta-aminophenols, meta-diphenols and certain heterocyclic compounds such as indole compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must be able to allow shades to be obtained in the desired intensity and it must show good resistance to external agents (light, bad weather, washing, waving, permanent-waving, perspiration, rubbing).

The dyes must also be able to cover grey hair and, lastly, they must be as unselective as possible, i.e. they must allow only the smallest possible colour differences to be obtained along the length of the same keratin fibre, which may, indeed, be differently sensitized (i.e. damaged) between tis tip and its root.

The Applicant has now discovered that it is possible to obtain novel, powerful, unselective and particularly resistant dyes, which are capable of giving rise to intense colorations in varied shades, by using imidazoloazole compounds as couplers in the presence of an oxidation base.

This discovery forms the basis of the present invention.

The subject of the invention is a composition for dyeing keratin fibres, and in particular human keratin fibres such as the hair, characterized in that it comprises, in a medium which is suitable for dyeing:

as coupler, at least one imidazoloazole compound of formula (I), or one of the addition salts thereof with an acid:

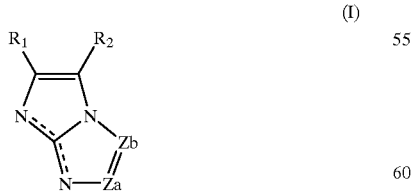

in which $R_1$ represents a hydrogen atom; a halogen atom (such as bromine, chlorine or fluorine); a linear or branched $C_1$–$C_5$ alkyl radical optionally substituted with one or two halogen, hydroxyl, alkoxy, aryloxy, amino, alkylamino, acyl or acylamino radicals; a $C_1$–$C_4$ alkoxy radical; a $C_1$–$C_4$ alkylthio radical; an arylthio radical; a benzylthio radical, an acyl radical; (such as acetyl; 3-phenylpropanoyl, benzoyl; 4-dodecyloxybenzoyl); an acylamino radical; an acyloxy radical; (such as acetoxy); a carbamoyl radical (such as carbamoyl; N-ethylcarbamoyl, N-phenylcarbamoyl, N,N-dibutylcarbamoyl); N-(2-dodecyloxyethyl) carbamoyl; a phenyl radical, optionally substituted with one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical (such as methoxycarbonyl, ethoxycarbonyl, isopropyloxycarbonyl, tert-butyloxycarbonyl, isobutyloxycarbonyl, butylcarbamoylethoxycarbonyl, perfluorohexylethoxycarbonyl; an aryloxycarbonyl radical (such as phenoxycarbonyl, 2,5-amylphenoxycarbonyl); a cyano radical; a nitro radical; a dialkylphosphinyl radical (such as dimethylphosphinyl); an alkylsulphinyl radical (such as 3-phenoxypropylsulphinyl); an arylsulphinyl radical (such as phenylsulphinyl); a sulphamoyl radical (such as N-ethylsulphamoyl, N,N-diisopropylsulphamoyl, N,N-diethylsulphamoyl); a carboxyl group; a sulpho group; an aryloxy radical (such as phenoxy, 2-methylphenoxy, 4-tert-butylphenoxy, 3-nitrophenoxy); a $C_1$–$C_4$ alkylamino radical; ureido (such as phenylureido, methylureido); sulphamoylamino (such as N,N-dipropylsulphamoylamino); an alkoxycarbonylamino radical (such as methoxycarbonylamino, ethoxycarbonylamino); a sulphonamido radical (such as methanesulphonamido, benzenesulphonamido, toluylsulphonamido); an aryloxycarbonylamino radical (such as phenoxycarbonylamino); a heteroarylthio (such as 2-benzothiazolylthio, 2-pyridylthio) a phosphonyl group (such as phenylphosphonyl);

$R_2$ represents: a hydrogen atom; a halogen atom such as bromine, chlorine or fluorine; an acetylamido group; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy, methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy, 1-naphthyloxy); an acyloxy radical (such as, for example: acetoxy, propanoyloxy, benzoyloxy, 2,4-dichlorobenzoyloxy, ethoxyalkyloxy, pyruvyloyloxy, cinnamoyloxy, myristoyloxy); an arylthio radical (such as, for example: phenylthio, 4-carboxyphenylthio, 2-ethoxy-5-tert-butylphenylthio, 2-carboxyphenylthio, 4-methanesulphonylphenylthio); an alkylthio radical (such as, for example: methylthio, ethylthio, propylthio, butylthio 2-cyanoethylthio, benzylthio, phenethylthio, 2-(diethylamino)ethylthio, ethoxyethylthio, phenoxyethylthio); a heteroarylthio radical (such as, for example: 5-phenyl-2,3,4,5-tetrazolylthio, 2-benzothiazolylthio); a heteroaryloxy radical (such as, for example: 5-phenyl-2,3,4,5-tetrazolyloxy, 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamido; an arylamido; and a radical $NR^{III}R^{IV}$ with $R^{III}$ and $R^{IV}$, which may be identical or different, representing a $C_1$–$C_4$ alkyl, a hydroxyalkyl; a carboxyl; or an alkyoxycarbonxylic radical;

$Z_a$ and $Z_b$ represent, independently of each other, a nitrogen atom or a carbon atom bearing a radical $R_3$ or $R_4$, with the proviso that at least one of the radicals $Z_a$ and $Z_b$ is a carbon atom;

$R_3$ and $R_4$ represent, independently of each other, a hydrogen atom; a halogen atom (such as bromine, chlorine or fluorine); a linear or branched $C_1$–$C_5$ radical optionally substituted with one or two halogen, hydroxyl, alkoxy, aryloxy, amino, alkylamino, acyl or acylamino radicals; an arylthio radical; an acyl radical (such as acetyl; 3-phenylpropanoyl, benzoyl; 4-dodecyloxybenzoyl); an acyloxy radical (such as acetoxy); a carbamoyl radical (such as carbamoyl; N-ethylcarbamoyl); a phenyl radical optionally substituted with one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical (such as methoxycarbonyl, ethoxycarbonyl, isopropyloxycarbonyl, tert-butyloxycarbonyl, isobutyloxycarbonyl, butylcarbamoylethoxycarbonyl, perfluorohexylethoxycarbonyl; an aryloxycarbonyl radical (such as phenoxycarbonyl, 2,5-amylphenoxycarbonyl); a cyano radical; a nitro radical; a dialkylphosphono radical (such as dimethylphosphono); a diarylphosphono radical (such as diphenylphosphono); a dialkylphosphinyl radical (such as dimethylphosphinyl); a diarylphosphinyl radical (such as diphenylphosphinyl); an alkylsulphonyl radical (such as 3-phenoxypropylsulphinyl); an arylsulphonyl radical (such as phenylsulphinyl); an arylsulphinyl radical (such as benzenesulphonyl, toluenesulphonyl); an alkylsulphonyl radical (methanesulphonyl, octanesulphonyl); a sulphonyloxy radical (such as methanesulphonyloxy, toluenesulphonyloxy); an acylthio radical (such as acetylthio, benzoylthio); a sulphamoyl radical (such as N-ethylsulphamoyl, N,N-diisopropylsulphamoyl, N,N-diethylsulphamoyl); a thiocyanate radical; a thiocarbonyl radical (such as methylthiocarbonyl, phenylthiocarbonyl); a haloalkylamino radical (such as N,N-di(trifluoromethylamino)); a heteroaryl (such as 2-benzoxazolyl, 2-benzothiazolyl; 5-chloro-1-tetrazolyl, 1-pyrrolyl, 2-furyl, 2-thienyl);

$R_3$ and $R_4$ can together form a substituted or unsubstituted aromatic ring (such as phenyl);

$R_5$ represents: a hydrogen atom; a linear or branched $C_1$–$C_{20}$ alkyl radical optionally substituted with one or two radicals R chosen from the group consisting of halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, acyl; an aryl radical (such as phenyl or naphthyl) optionally substituted with one or two radicals R as defined above; a 5- or 6-membered heterocycle having at least one nitrogen, oxygen or sulphur atom (such as pyridyl, quinolyl, pyrrolyl, morpholyl, furyl, tetrahydrofuryl, pyrazolyl, triazolyl, tetrazolyl, thiazolyl, oxazolyl, imidazolyl or thiadiazolyl) optionally substituted with one or two radicals R as defined above;

$R_5$ denotes an alkyl radical, an aryl radical or a 5- or 6-membered heterocycle (defined above), it can be linked to the carbon atom of the ring via an oxygen, nitrogen or sulphur atom (in this case, $R_5$ becomes $XR_5$ with X=O, NH, S);

$R_5$ can also denote a halogen atom (such as bromine, chlorine or fluorine); an acyl radical; a sulphonyl radical; a sulphinyl radical; a phosphonyl radical, a carbamoyl radical; a sulphamoyl radical; a cyano radical; a siloxy radical, an amino radical; an acylamino radical; an acyloxy radical; a carbamoyloxy radical; a sulphonamide radical; an imide radical; a ureido radical; a sulphamoylamino radical; an alkoxycarbonylamino radical; an aryloxycarbonyl amino radical; an alkoxycarbonyl radical; an aryloxycarbonyl radical; a carboxyl radical;

and at least one oxidation base.

The addition salts with an acid for the compounds of the invention can be chosen in particular from hydrochlorides, hydrobromides, tartrates, tosylates, benzenesulphonates, sulphates, lactates and acetates.

Among the radicals $R_1$ of formula (I) defined above, the preferred radicals are chosen from the group consisting of: hydrogen, $C_1$–$C_4$ alkyl; phenyl; phenyl substituted with a chlorine, a bromine, a nitro, a sulphonyl group, $C_1$–$C_4$ alkoxy, $C_1$–$C_4$ alkyl, a $C_1$–$C_3$ trifluoroalkyl, an amino or a $C_1$–$C_4$ alkylamino; acyl; acyloxy; carbamoyl; alkoxycarbonyl, aryloxycarbonyl; cyano; nitro; alkylsulphinyl; arylsulphinyl; sulphamoyl; haloalkyl.

Among the radicals $R_1$ of formula (I), the radicals more particularly preferred are chosen from the group consisting of:

hydrogen, $C_1$–$C_4$ alkyl (such as methyl, ethyl, propyl, isopropyl, tert-butyl); phenyl; phenyl substituted with a chlorine, a sulphonyl, a methoxy, an ethoxy, a $C_1$–$C_4$ alkyl or a trifluoromethyl group; acyl (such as acetyl, ethylcarbonyl, phenylcarbonyl); cyano; alkoxycarbonyl (such as methoxycarbonyl, ethoxycarbonyl); carbamoyl (such as carbamoyl; N-ethylcarbamoyl); trifluoromethyl.

Even more particularly, the preferred radicals $R_1$ are chosen from the group consisting of:

hydrogen; methyl, ethyl or isopropyl; phenyl; phenyl substituted with a chlorine, a methyl or a methoxy; cyano; methoxycarbonyl or ethoxycarbonyl.

Among the radicals $R_2$ of formula (I) defined above, the preferred radicals are chosen from the group consisting of: a hydrogen atom; a $C_1$–$C_4$ alkoxy; phenoxy; phenoxy substituted with a halogen atom, a $C_1$–$C_4$ alkyl, a carboxyl, a trifluoromethyl group; an acyloxy radical; benzyloxy; $C_1$–$C_4$ alkylthio; phenylthio; phenylthio substituted with a halogen atom, a $C_1$–$C_4$ alkyl, a carboxyl, a trifluoromethyl group; a $C_1$–$C_4$ alkylamido; phenylamido; a radical $NR^{II}R^{IV}$ with $R^{III}$ and $R^{IV}$, which may be identical or different, representing a $C_1$–$C_4$ alkyl, a $C_1$–$C_4$ hydroxyalkyl; a carboxyl; a $C_1$–$C_4$ alkoxycarbonylic radical.

Among the radicals $R_2$ of formula (I) defined above, the radicals more particularly preferred are chosen from the group consisting of:

hydrogen; chlorine or bromine; methoxy or ethoxy; phenoxy; 4-methylphenoxy; acyloxy; benzyloxy; methylthio or ethylthio; phenylthio; 4-methylphenylthio; 2-tert-butylphenylthio; acetamido; phenylacetamido; dimethylamino; diethylamino; ethylmethylamino; (β-hydroxyethyl) methylamino.

Even more particularly, the preferred radicals $R_2$ are chosen from the group consisting of:

hydrogen; chlorine; ethoxy; phenoxy; benzyloxy; acyloxy; acetamido; dimethylamino.

Among the radicals $R_3$ and $R_4$ of formula (I), the preferred radicals are chosen from the group consisting of:
acyl; acyloxy; carbamoyl; alkoxycarbonyl; aryloxycarbonyl; cyano; nitro; alkylsulphinyl; arylsulphinyl; alkylsulphonyl; arylsulphonyl; haloalkyl; aryl; heteroaryl; hydrogen; $C_1$–$C_4$ alkyl; carboxyl; hydrogen.

Among the radicals $R_3$ and $R_4$ of formula (I), the radicals more particularly preferred are chosen from the group consisting of: alkoxycarbonyl (such as methoxycarbonyl, ethoxycarbonyl); aryloxycarbonyl (such as phenoxycarbonyl, chlorophenoxycarbonyl, toluyloxycarbonyl); nitro; cyano; arylsulphonyl (such as phenylsulphonyl); carbamoyl (such as carbamoyl; N-ethylcarbamoyl); haloalkyl (such as trifluoromethyl); carboxyl; hydrogen; methyl; ethyl or isopropyl; hydrogen.

Even more particularly, the preferred radicals $R_3$ and $R_4$ are chosen from the group consisting of:
cyano; trifluoromethyl; methoxycarbonyl; ethoxycarbonyl; phenoxycarbonyl; hydrogen; methyl or ethyl; carboxyl.

Among the radicals $R_5$ of formula (I) defined above, the preferred radicals are chosen from the group consisting of:
a hydrogen atom; a linear or branched $C_1$–$C_4$ alkyl; a trifluoromethyl radical; a phenyl; a phenyl substituted with one or two groups chosen from a halogen, a $C_1$–$C_4$ alkyl, a $C_1$–$C_4$ alkoxy, a hydroxyl, a carboxyl, a nitro group, a $C_1$–$C_4$ alkylthio, a methylenedioxy group, an amino group, a trifluoromethyl group or a $C_1$–$C_4$ alkylamino; a benzyl radical; a benzyl radical substituted with a halogen atom, a methyl or isopropyl, methoxy; a $C_1$–$C_4$ hydroxyalkyl; a $C_1$–$C_4$ aminoalkyl; a $C_1$–$C_4$ alkylaminoalkyl; an alkoxy radical chosen from methoxy, ethoxy, and phenoxy; methylthio; ethylthio; phenylthio; methanesulphonyl.

Among the radicals $R_5$ of formula (I) defined above, the radicals more particularly preferred are chosen from the group consisting of: hydrogen; an alkyl chosen from methyl, ethyl, isopropyl, n-propyl, tert-butyl; phenyl; toluyl; 2-, 3- or 4-chlorophenyl; 3- or 4-hydroxyphenyl; 3- or 4-aminophenyl; 3- or 4-methoxyphenyl; 4-trifluoromethylphenyl; benzyl; trifluoromethyl; hydroxymethyl; hydroxyethyl; hydroxyisopropyl; aminomethyl or aminoethyl; methoxy or ethoxy; methylthio or ethylthio.

Even more particularly, the preferred radicals $R_5$ are chosen from the group consisting of:
hydrogen; methyl; ethyl; isopropyl; phenyl; 4-chlorophenyl; 4-methoxyphenyl; 4-aminophenyl; methoxy or ethoxy; methylthio or ethylthio.

Among the preferred compounds of the invention of formula (I), mention may be made of those chosen from the group consisting of:
(i) imidazolo[3,2-a]imidazoles of formula:

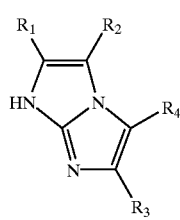

(Ia)

(ii) imidazolo[1,2-b]-1,2,4-triazoles of formula:

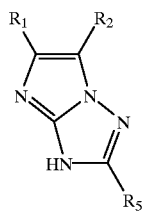

(Ib)

(iii) imidazolo[2,1-c]-1,2,4-triazoles of formula:

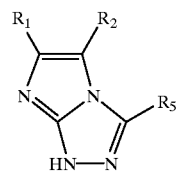

(Ic)

in which $R_1$, $R_2$, $R_3$, $R_4$ and $R_5$ have the same meanings as those given above in formula (I).

As examples of compounds of formula (Ia), mention may be made of those for which:
$R_1$ denotes hydrogen, methyl, ethyl, isopropyl or phenyl;
$R_2$ denotes hydrogen or chlorine;
$R_3$ and $R_4$ respectively denote cyano and cyano; carboxyl and carboxyl or methoxycarbonyl and cyano.

As compounds of formula (Ia) above, mention may be made most particularly of:
7,8-dicyanoimidazolo[3,2-a]imidazole,
7,8-dicyano-4-methylimidazolo[3,2-a]imidazole,
7,8-dicyano-4-ethylimidazolo[3,2-a]imidazole,
7,8-dicyano-4-isopropylimidazolo[3,2-a]imidazole,
7,8-dicyano-4-phenylimidazolo[3,2-a]imidazole,
5-chloro-7,8-dicyano-4-methylimidazolo[3,2-a] imidazole,
7,8-dicyano-4-trifluoromethylimidazolo[3,2-a]imidazole, and the addition salts thereof with an acid.

As examples of compounds of formula (Ib), mention may be made of those for which:
$R_1$ denotes hydrogen, methyl, ethyl, isopropyl or phenyl;
$R_2$ denotes hydrogen or chlorine;
$R_5$ denotes hydrogen, methyl, ethyl, phenyl, toluyl or trifluoromethyl.

As compounds of formula (Ib) above, mention may be made most particularly of:
imidazolo[1,2-b]-1,2,4-triazole,
6-methylimidazolo[1,2-b]-1,2,4-triazole,
6-isopropylimidazolo[1,2-b]-1,2,4-triazole,
6-phenylimidazolo[1,2-b]-1,2,4-triazole,
2,6-dimethylimidazolo[1,2-b]-1,2,4-triazole,
6-isopropyl-2-methylimidazolo[1,2-b]-1,2,4-triazole,
2-methyl-6-phenylimidazolo[1,2-b]-1,2,4-triazole,
6-methyl-2-phenylimidazolo[1,2-b]-1,2,4-triazole,
6-isopropyl-2-phenylimidazolo[1,2-b]-1,2,4-triazole,
7-chloro-2,6-dimethylimidazolo[1,2-b]-1,2,4-triazole,
7-chloro-2-phenyl-6-tertbutylimidazolo[1,2-b]-1,2,4-triazole, 6-trifluoromethylimidazolo[1,2-b]-1,2,4-triazole,
and the addition salts thereof with an acid.

As examples of compounds of formula (Ic), mention may be made of those for which:
- $R_1$ denotes hydrogen, methyl, ethyl, isopropyl or phenyl;
- $R_2$ denotes hydrogen or chlorine;
- $R_5$ denotes hydrogen, methyl, ethyl, phenyl, toluyl or trifluoromethyl.

As compounds of formula (Ic) above, mention may be made most particularly of:
imidazolo[2,1-c]-1,2,4-triazole,
5-methylimidazolo[2,1-c]-1,2,4-triazole,
5,8-dimethylimidazolo[2,1-c]-1,2,4-triazole,
5-methyl-8-phenylimidazolo[2,1-c]-1,2,4-triazole,
8-phenylimidazolo[2,1-c]-1,2,4-triazole,
6-chloro-5,8-dimethylimidazolo[2,1-c]-1,2,4-triazole,
and the addition salts thereof with an acid.

The compounds of the present invention, their synthetic intermediates and processes for their preparation are described in the patents and patent applications U.S. Pat. No. 5,441,863; JP 62-279,337; JP 60-236,011 and JP 07-092,632.

The compound(s) of formula (I) preferably represent(s) from 0.0005 to 12% by weight approximately relative to the total weight of the dye composition, and even more preferably from 0.005 to 6% by weight approximately relative to this weight.

The nature of the oxidation base(s) which can be used in the dye composition according to the invention is not critical. This or these oxidation bases is(are) preferably chosen from para-phenylenediamines, bis(phenyl)alkylenediamines, para-aminophenols, ortho-aminophenols and heterocyclic bases, and the addition salts thereof with an acid.

Among the para-phenylenediamines which can be used as oxidation bases in the dye composition according to the invention, mention may be made in particular of the compounds corresponding to formula (II) below, and the addition salts thereof with an acid:

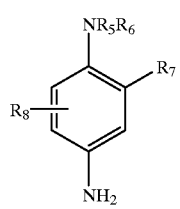

(II)

in which:
- $R_5$ represents a hydrogen atom, a $C_1$–$C_4$ alkyl, $C_1$–$C_4$ monohydroxyalkyl, $C_2$–$C_4$ polyhydroxyalkyl or ($C_1$–$C_4$)alkoxy($C_1$–$C_4$)alkyl radical,
- $R_6$ represents a hydrogen atom or a $C_1$–$C_4$ alkyl, $C_1$–$C_4$ monohydroxyalkyl or $C_2$–$C_4$ polyhydroxyalkyl radical,
- $R_7$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical,
- $R_8$ represents a hydrogen atom or a $C_1$–$C_4$ alkyl radical.

In formula (II) above, and when $R_7$ is other than a hydrogen atom, then $R_5$ and $R_6$ is preferably represent a hydrogen atom and $R_7$ is preferably identical to $R_8$, and when $R_7$ represents a halogen atom, then $R_5$, $R_6$ and $R_8$ preferably represent a hydrogen atom.

Among the para-phenylenediamines of formula (II) above, mention may be made more particularly of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl) aminobenzene and 2-chloro-para-phenylenediamine, and the addition salts thereof with an acid.

Among the bis(phenyl)alkylenediamines which can be used as oxidation bases in the dye composition according to the invention, mention may be made in particular of the compounds corresponding to formula (III) below, and the addition salts thereof with an acid:

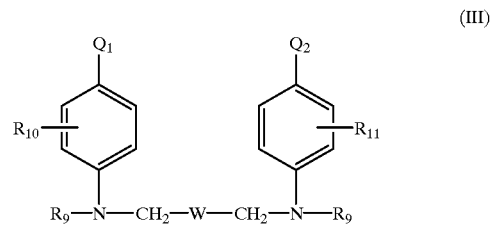

(III)

in which:
- $Q_1$ and $Q_2$, which may be identical or different, represent a hydroxyl radical or a radical $NHR_{12}$ in which $R_{12}$ represents a hydrogen atom or a $C_1$–$C_4$ alkyl radical,
- $R_9$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amino residue may be substituted,
- $R_{10}$ and $R_{11}$, which may be identical or different, represent a hydrogen or halogen atom or a $C_1$–$C_4$ alkyl radical,
- W represents a radical taken from the group consisting of the following radicals $$-(CH_2)_n-;\ -(CH_2)_m-O-(CH_2)_m;\ -(CH_2)_m-CHOH-(CH_2)_m$$

$$-(CH_2)_{\overline{m}}-\underset{\underset{CH_3}{|}}{N}-(CH_2)_{\overline{m}}-;$$

in which n is an integer between 0 and 8 inclusive and m is an integer between 0 and 4 inclusive.

Among the bis(phenyl)alkylenediamines of formula (III) above, mention may be made more particularly of N,N'-bis (β-hydroxyethyl-N,N'-bis-(4'-aminophenyl)-1,3-diamino-2-propanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine and N,N'-bis (ethyl)-N,N'-bis(4'-amino-3'-methylphenyl) ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid is particularly preferred.

Among the para-aminophenols which can be used as oxidation bases in the dye composition according to the invention, mention may be made in particular of the compounds corresponding to formula (IV) below, and the addition salts thereof with an acid;

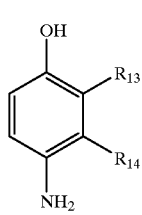

(IV)

in which:
R$_{13}$ represents a hydrogen atom or a C$_1$–C$_4$ alkyl, C$_1$–C$_4$ monohydroxyalkyl, (C$_1$–C$_4$)alkoxy(C$_1$–C$_4$)alkyl or C$_1$–C$_4$ aminoalkyl radical,
R$_{14}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, cyano(C$_1$–C$_4$) alkyl or
(C$_1$–C$_4$)alkoxy(C$_1$–C$_4$)alkyl radical, it being understood that at least one of the radicals R$_{13}$ or R$_{14}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dye composition according to the invention, mention may be made in particular of 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases which can be used as oxidation bases in the dye composition according to the invention, mention may be made in particular of pyridine derivatives, pyrimidine derivatives and pyrazole derivatives, and the addition salts thereof with an acid.

Among the pyridine derivatives, mention may be made more particularly of the compounds described, for example, in GB patent 1,026,978 and 1,153,196, such as 2,5-diaminopyridine, and the addition salts thereof with an acid.

Among the pyrimidine derivatives, mention may be made more particularly of compounds described, for example, in German patent DE 2,359,399 or Japanese patents JP 88-169, 571 and JP 91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE 3,843,892 and DE 4,133,957 and patent applications WO 94/08969 and WO 94/08970, such as 4,5-diamino-1-methylpyrazole and 3,4-diaminopyrazole, and the addition salts thereof with an acid, and 1-(4'-chlorobenzyl)-4,5-diaminopyrazole.

According to the invention, the oxidation base(s) preferably represent(s) from 0.0005 to 12% by weight approximately relative to the total weight of the dye composition, and even more preferably from 0.005 to 6% by weight approximately relative to this weight.

The dye composition according to the invention can also contain one or more additional couplers other than compounds of formula (I) and/or one or more direct dyes, so as to vary the shades obtained with the oxidation bases or to enrich the shades with glints.

The additional couplers which can be used in the composition according to the invention can be chosen from the couplers used conventionally in oxidation dyeing, and among which mention may be made in particular of meta-phenylenediamines, meta-aminophenols, meta-diphenols and heterocyclic couplers such as, for example, indole derivatives and indolene derivatives, and addition salts thereof with an acid.

These couplers can be chosen in particular from 2-methyl-5-aminophenol, 5-N-(β-hydroxyethyl)amino-2-methylphenol, 3-aminophenol, 1,3-dihydoxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindolene, and the addition salts thereof with an acid.

When they are present, these additional couplers preferably represent from 0.0005 to 5% by weight approximately relative to the total weight of the dye composition, and even more preferably from 0.005 to 3% by weight approximately relative to this weight.

The addition salts with an acid for the oxidation base(s) and/or for the additional couplers which can be used in the dye composition of the invention are chosen in particular form the hydrochlorides, hydrobromides, sulphates, tartrates, lactates and acetates.

The medium which is suitable for dyeing (or the support) generally consists of water or of a mixture of water and at least one organic solvent for dissolving the compounds which would not be sufficiently water-soluble. As organic solvents, mention may be made, for example, of C$_1$–C$_4$ lower alcohols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1% and 40% by weight approximately relative to the total weight of the dye composition, and even more preferably between 5 and 30% by weight approximately.

The pH of the dye composition in accordance with the invention is generally between 3 and 12. It can be adjusted to the desired value using acidifying or basifying agents usually used to dye keratin fibres.

Among the acidifying agents, mention may be made, by way of example, of inorganic or organic acids such as hydrochloric acid, orthophosphoric acid, carboxylic acids such as tartaric acid, citric acid and lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (V) below:

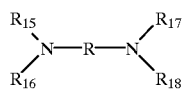
(V)

in which R is a propylene residue optionally substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

The dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, the person skilled in the art will take care to select the optional complementary compound(s) mentioned above, such that the advantageous properties intrinsically associated with the dye composition according to the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The subject of the invention is also the use of the imidazoloazoles of formula (I) above, as couplers, in combination with at least one oxidation base for the oxidation dyeing of keratin fibres, and in particular human keratin fibres such as the hair.

Another subject of the invention is a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition only at the moment of use, or which is present in an oxidizing composition that is applied simultaneously or sequentially in a separate manner.

According to a particularly preferred embodiment of the dyeing process according to the invention, the dye composition described above is mixed, at the moment of use, with an oxidizing composition containing, in a medium which is suitable for dyeing, at least one oxidizing agent that is present in an amount which is sufficient to develop a coloration. The mixture obtained is then applied to the keratin fibres and is left to stand on them for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that after mixing with the dye composition, the pH of the resulting composition applied to the keratin fibres preferably ranges between 3 and 12 approximately and even more preferably between 5 and 11. It is adjusted to the desired value using acidifying or basifying agents usually used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a dyeing "kit" or multi-compartment device or any other multi-compartment packaging system in which a first compartment contains the dye composition as defined above and a second compartment contains the oxidizing composition as defined above.

These devices can be equipped with means which allow the desired mixture to be delivered into the hair, such as the devices described in patent FR-2,586,913 in the name of the Applicant.

EXAMPLES

Dyeing Example 1

The following dye composition, in accordance with the invention, was prepared:

| | |
|---|---|
| Para-phenylenediamine | 0.324 g |
| 7,8-Dicyano-4-methylimidazolo-[3,2-a]imidazole (coupler of formula (I) in accordance with the invention | 0.513 g |
| Benzyl alcohol | 2.0 g |
| Polyethylene glycol containing 6 mol of ethylene oxide | 3.0 g |
| Ethyl alcohol | 20.0 g |
| ($C_8$ $C_{10}$) Alkylpolyglucoside as an aqueous solution containing 60% active material, buffered with ammonium citrate, sold under the name Oramix CG110 by the company SEPPIC | 6.0 g |
| Aqueous ammonia containing 20% $NH_3$ | 10.0 g |
| Sodium metabisulfite | 0.228 g |
| Sequestering agent | q.s. |
| Demineralized water q.s. | 100.0 g |

NB: The 7,8-dicyano-4-methylimidazolo[3,2-a]imidazole was prepared according to the synthetic process described in U.S. Pat. No. 5,441,863.

At the moment of use, the dye composition defined above was mixed with an equal weight of 20-volumes of hydrogen peroxide solution (6% by weight).

The mixture obtained has a pH of 10.1, and was applied for 30 minutes to locks of permanent-waved or non-permanent-waved natural grey hair containing 90% white hairs, at a rate of 10 g per 1 g of hair. After rinsing, washing with a standard shampoo and drying, the locks were dyed in the shades featured in the table below:

| Example | Shade obtained on natural grey hair containing 90% white hairs | Shade obtained on permanent-waved grey hair containing 90% white hairs |
|---|---|---|
| 1 | slightly golden natural | slightly iridescent |

Dyeing Example 2

A dye composition identical to the one described for Example 1 above was prepared.

At the moment of use, this dye composition was mixed with an equal weight-amount of aqueous ammonium persulphate solution at a concentration of $6 \times 10^{-3}$ mol %.

The mixture obtained had a pH of 9.8, and was applied for 30 minutes to locks of natural grey hair containing 90% white hairs, at a rate of 10 g per 1 g of hair. After rinsing, washing with a standard shampoo and drying, the locks were dyed in a golden shade.

What is claimed is:

1. A process for the oxidation dyeing of keratin fibers comprising
   (a) applying to the keratin fibers an effective amount for dyeing of at least one dyeing composition;
   (b) developing color at acidic, neutral, or alkaline pH in presence of an oxidizing agent which is added to said at least one dyeing composition at the same time said at least one dyeing composition is applied, or which is present in an oxidizing composition that is applied:
      (i) separately from said at least on dyeing composition at the same time that said at least one dyeing composition is applied to the fibers, or
      (ii) sequentially with said at least one dyeing composition,
   wherein said at least one dyeing composition comprises, in a medium which is suitable for dyeing, at least one oxidation base and at least one coupler chosen from imidazoloazole compounds of formula (I) and acid addition salts thereof;

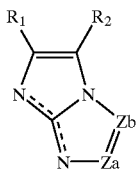

(I)

in which:
$R_1$ is chosen from a hydrogen atom; a halogen atom; a linear or branched $C_1$–$C_5$ alkyl radical, unsubstituted or substituted with one or two halogen, hydroxyl, alkoxy, aryloxy, amino, alkylamino, acyl or acylamino radicals; a $C_1$–$C_4$ alkoxy radical; a $C_1$–$C_4$ alkylthio radical; an arylthio radical; a benzylthio radical, an acyl radical; an acylamino radical; an acyloxy radical; a carbamoyl radical; a phenyl radical, unsubstituted or substituted with one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical; an aryloxycarbonyl radical; a cyano radical; a nitro radical; a dialkylphosphinyl radical; an arylsulphinyl radical; an alkylsulphinyl radical; a sulphamoyl radical; a carboxyl group; a sulpho group; an aryloxy radical; a $C_1$–$C_4$ alkylamino radical; a ureido radical; a sulphamoylamino radical; a sulphonamido radical; an alkoxycarbonylamino radical; an aryloxycarbonylamino radical; a heteroarylthio radical; and a phosphonyl group;

$R_2$ is chosen from a hydrogen atom; a halogen atom; an acetylamido group; an alkoxy radical; an aryloxy radical; an acyloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1, 2-dihydro-1-pyridyl radical; an alkylamido; an arylamino; and a radical $NR^{III}R^{IV}$ wherein $R^{III}$ and $R^{IV}$ are independently chosen from a $C_1$–$C_4$ alkyl, a hydroxyalkyl, a carboxyl, and an alkyoxycarbonxylic radical;

$Z_a$ and $Z_b$ independently are chosen from a nitrogen atom and a carbon atom bearing a radical $R_3$, $R_4$ and $R_5$, with the proviso that at least one of $Z_a$ and $Z_b$ is a carbon atom;

$R_3$ and $R_4$ independently are chosen from a hydrogen atom; a halogen atom; a linear or branched $C_1$–$C_5$ alkyl radical, unsubstituted or substituted with one or two halogen, hydroxyl, alkoxy, aryloxy, amino, alkylamino, acyl or acylamino radicals; an arylthio radical; an acyl radical; an acyloxy radical; a carbamoyl radical; a phenyl radical, unsubstituted or substituted with one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical; an aryloxycarbonyl radical; a cyano radical; a nitro radical; a dialkylphosphono radical; a diarylphosphono radical; a dialkylphosphinyl radical; a diarylsulphonyl radical; an alkylsulphinyl radical; an arylsulphinyl radical; an arylsulphonyl radical; an alkylsulphonyl radical; a sulphonyloxy radical; an acylthio radical; a sulphamoyl radical; a thiocyanate radical; a thiocarbonyl radical; a haloalkylamino radical; and a heterocycle; or $R_3$ and $R_4$ can together form a substituted or unsubstituted aromatic ring;

$R_5$ is chosen from a hydrogen atom; a linear or branched $C_1$–$C_{20}$ alkyl radical, unsubstituted or substituted with one or two radicals R; an aryl radical, unsubstituted or substituted with one or two radicals R; and a 5- or 6-membered heterocycle having at least one nitrogen, oxygen or sulphur atom, unsubstituted or substituted with one or two radicals R;

wherein R is chosen from halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, and acyl groups; and wherein when $R_5$ is an alkyl radical, aryl radical or 5- or 6-membered heterocycle, $R_5$ is linked to the carbon atom of the ring via an oxygen, nitrogen or sulphur atom so that $R_5$ becomes $XR_5$, wherein X is O, NH, or S; and $R_5$ can also be chosen from a halogen atom; an acyl radical; a sulphonyl radical; a sulphinyl radical; a phosphonyl radical, a carbamoyl radical; a sulphamoyl radical; a cyano radical; a siloxy radical, an amino radical; an acylamino radical; an acyloxy radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; and a carboxyl radical.

2. A process according to claim 1, wherein said keratin fibers are human hair.

3. A process according to claim 1, wherein said oxidizing agent is hydrogen peroxide, urea peroxide, an alkali metal bromate, or a persalt.

4. A process according to claim 3, wherein said persalt is a perborate or persulphate.

5. A process according to claim 3, wherein said oxidizing agent is hydrogen peroxide.

6. A process according to claim 1, wherein before said applying step, mixing said at least one composition with an oxidizing composition comprising, in a medium suitable for dyeing, at least one oxidizing agent in an amount sufficient to develop coloration; and after said developing step, leaving said mixture on said keratin fibers for a time ranging from 3 to 50 minutes; and rinsing, washing, rinsing again, and drying said keratin fibers.

7. A process according to claim 6, wherein the mixture is left on said keratin fibers for a time ranging from 5 to 30 minutes.

* * * * *

UNITED STATES PATENT AND TRADEMARK OFFICE
CERTIFICATE OF CORRECTION

PATENT NO.: 6,165,229

DATED: December 26, 2000

INVENTOR(S): Vidal et al.

It is certified that errors appear in the above-identified patent and that said Letters Patent is hereby corrected as shown below:

Claim 1, col. 14, line 42, delete "diarylsulphonyl" and replace with - - diarylphosphinyl- -.

Signed and Sealed this

First Day of May, 2001

*Attest:*

NICHOLAS P. GODICI

*Attesting Officer*     *Acting Director of the United States Patent and Trademark Office*